United States Patent [19]

Warner

[11] Patent Number: 5,709,699

[45] Date of Patent: Jan. 20, 1998

[54] BLOOD COLLECTION AND TESTING DEVICE

[75] Inventor: Henry A. Warner, Lake Forest, Ill.

[73] Assignee: BioSafe Diagnostics Corporation, Lincolnshire, Ill.

[21] Appl. No.: 515,080

[22] Filed: Sep. 1, 1995

[51] Int. Cl.$^6$ ........................................... A61B 17/32
[52] U.S. Cl. ........................................... 606/181
[58] Field of Search .................. 128/760, 771; 606/181–183

[56] References Cited

U.S. PATENT DOCUMENTS

| | | | |
|---|---|---|---|
| 4,230,118 | 10/1980 | Holman | 128/314 |
| 4,469,110 | 9/1984 | Slama | 128/770 |
| 4,503,856 | 3/1985 | Cornell et al. | 128/314 |
| 4,653,513 | 3/1987 | Dombrowski | 128/765 |
| 4,844,098 | 7/1989 | Mitchen | 128/765 |
| 5,014,718 | 5/1991 | Mitchen | 128/771 |
| 5,035,704 | 7/1991 | Lambert et al. | 606/182 |
| 5,070,886 | 12/1991 | Mitchen et al. | 128/771 |
| 5,231,993 | 8/1993 | Haber et al. | 128/770 |
| 5,274,240 | 12/1993 | Mathies et al. | 250/458.1 |
| 5,402,798 | 4/1995 | Swierczek et al. | 128/770 |

FOREIGN PATENT DOCUMENTS

| | | |
|---|---|---|
| 0164148 | 12/1985 | European Pat. Off. . |
| 2909349 | 9/1980 | Germany . |
| 8504089 | 9/1985 | United Kingdom . |

*Primary Examiner*—Max Hindenburg
*Attorney, Agent, or Firm*—Banner & Witcoff, LTD.

[57] ABSTRACT

This invention relates to a blood collection device and method of use. The device comprises a resilient cup with a top for receiving the patient's skin or finger. The top of cup bunches or pinches the skin to increase its surface tension thereby providing a relativity painless piercing by a lancet within the cup. The lancet is supported by a bushing to provide a true cut into the skin without movement of the lancet. The method comprises a safe, relatively painless procedure for collecting blood and transferring it to a test medium for diagnostic purposes.

9 Claims, 3 Drawing Sheets

BLOOD COLLECTION AND TESTING DEVICE

FIELD OF THE INVENTION

The present invention relates to a device for drawing a small amount of blood for collection and testing. More particularly, the invention relates to a single use device and a method for obtaining a blood sample and testing the blood sample.

DESCRIPTION OF THE PRIOR ART

Blood samples can be obtained by merely pricking the finger tip or skin surface with a sharp tool. The samples are subsequently exposed to a proper test medium to obtain results. Previously, a variety of complex, sudden release, pen type devices with disposable needles were used to perforate the skin.

Conventional devices perform a finger stick procedure using a spring loaded apparatus to thrust a lancet into a fingertip at high speed. A lancet is loaded in the device and the action is cocked, the finger to be pierced is held against a platform, and a button is pushed releasing the spring loaded action and piercing the finger automatically. Examples of these devices include the Monojector (U.S. Pat. No. 4,503,856) manufactured by Monoject Company, the Autolet (U.S. Pat. No. 4,230,118), manufactured by Owen Mumford Limited, and similar devices by Becton Dickenson, Bio-Dynamics, and others.

All of these devices pierce the skin automatically but rely upon the subject or technician to force the blood from the puncture site by squeezing the fingertip. This milking action can be painful. Dombrowski (U.S. Pat. No. 4,653,513) seeks to reduce the pain and eliminate the need for milking the blood from the puncture site by the use of vacuum to collect a droplet of blood. The apparatus disclosed would also permit blood collection from a less vascularized area. However, the devices make a conventional puncture which yields a substantial amount of blood (up to 0.5 milliliters), more that is required for many diagnostic tests. The excess blood, which may be contaminated with any of a number of infectious agents such as Hepatitis A, B, and C, or HTLV of Acquired Immune Deficiency, must then be disinfected thereby exposing the technicians performing this procedure to the risk of infection.

Conventional lancing devices (including Dombrowski) address acquisition of the blood sample. That sample must then be transported to the site where the diagnostic test will be performed. The samples may then be processed in a variety of ways before the diagnostic test is performed. Once the test is performed, the test system and the contaminated collection devices must be disposed of, frequently, by inconvenient methods. In addition, the blood samples that are delivered to the testing site are not uniform.

Hutcheson (European Patent Application, 0164148, Dec. 11, 1985), disclosed a device where the diagnostic test system and lance are contained within a kit, whereby the subject is lanced and then immediately transfers a sufficient amount of blood to the test strip.

Palmer (International Application WO 85/04089, Sep. 26, 1985), disclosed a device and method for the simultaneous collection and processing of a blood sample. The apparatus disclosed in Palmer comprises a puncturing device within a chamber containing a liquid which is the reagent system employed by the test. Palmer addresses the simultaneous collection and processing of a blood sample. However the device can only be used for tests with liquid reagents which are stable for long periods of time in liquid form. Because such liquid reagent systems are not typically stable at room temperature very long, this limits the practical application of such a system. The puncture employed by Palmer is a conventional puncture such as that employed by Monoject, Autolet, and others, which will leave a wound site which must be disinfected and covered until bleeding has ceased.

U.S. Pat. Nos. 5,070,866 and 5,014,718 describe finger stick devices which are a base with a needle mounted on the base and a flexible cup also is mounted on the base. The flexible cup has an opening at the top with a finger rest device. These patents describe simultaneous skin puncture and bleeding directly onto internal filter paper, but this device only collects a single small ¼" diameter blood spot which is insufficient for testing. Typical blood spot tests are accomplished on 3 or more ½" diameter spots, or over 12 times as much blood as the device described in these patents collects. Also there are questions about how the blood would diffuse through a small spot. This device also thrusts the lancet through the solid center of the filter paper causing the patient to push harder, possibly dulling the sharp before it enters the skin, distorting the paper with the puncture and compressing the filter paper. The lancet may experience lateral movement and not produce a sharp, clean incision for bleeding. These devices have a very short travel time, about the same distance as lancet penetration depth, little or no vacuum (and very small volume of blood), and almost imperceptible snap-action which occurs after the lancet starts to puncture the skin.

SUMMARY OF THE INVENTION

It is an object of the present invention to provide a blood sampling device comprising a base, a cover hingedly attached to the base, a resilient cup mounted on the base, an opening at the top of the resilient cup for placing a finger or skin surface to be lanced and a bushing surrounding the lancet to stabilize it when it is compressed while piercing the skin. The device allows for the bunching or pinching of the skin by placement of the skin over the opening at the top of the cup to increase the surface tension of the skin and to minimize the pain upon piercing with the lancet. The device includes a bushing surrounding the lancet to stabilize the lancet and to help control the depth of penetration of the lancet into the skin. Further, the lancet is enclosed within a resilient cup and encapsulated within a housing for safe shipment and disposal. The position of the lancet within the resilient cup and housing nearly obliterates the view of the lancet from the patient, thereby reducing trauma.

It is another object of the present invention to disclose a safe, minimally-invasive, relatively painless method for the collection and testing of blood for specific components.

Briefly stated, the method of the present invention comprises pre-treating the external surface of an area of the skin of a human or animal to anesthetize and to make antiseptic; bunching or squeezing the area of the skin to be pierced, piercing the skin in that area without significant pain, collecting a sample comprising blood and body fluids from the area and applying them to a medium for testing. The sample can then be tested for one or more diagnostic purposes. The procedure is relatively painless.

The present invention is an improvement in the mechanisms disclosed in U.S. Pat. Nos. 5,070,866 and 5,014,718. The present invention allows for the safe, relatively painless puncturing of the skin so that blood may be obtained. The blood of the patient is then moved to filter paper where specimens can be deposited in a designated area for testing.

In the present invention the skin or finger of the patient is placed on the top of the resilient cup, downward pressure is applied to bunch or squeeze the skin within the opening at the top of the cup. The pressure compresses the cup so that the bottom of the cup flattens and moves outwardly due to the compression of the cup. The lancet which is surrounded by a bushing remains rigid and thereby pierces the skin so that blood flow may commence. The bunching or squeezing of the skin cause blood to flow profusely upon piercing so that there is an adequate amount for testing.

The above is a brief description of some deficiencies in the prior art and advantages of the present invention. Other features, advantages and embodiments of the invention will be apparent to those skilled in the art from the foregoing description, accompanying drawings and appended claims.

DETAILED DESCRIPTION OF THE INVENTION

Figure 1:
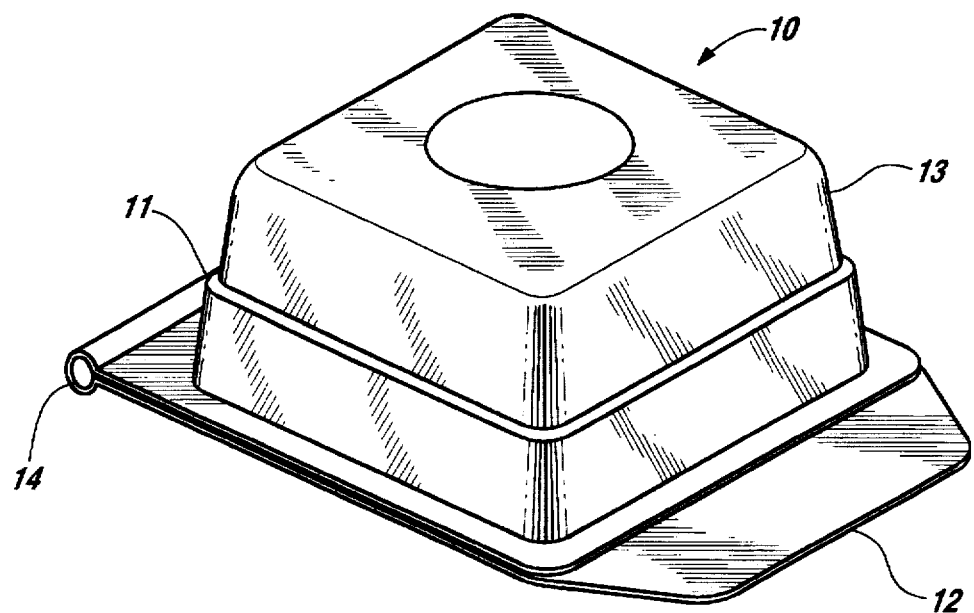
FIG. 1 is a perspective view of the apparatus of the present invention packaged prior to use.

Referring to the drawings, it can be seen that a device according to the invention 10 is shown in a perspective view in FIG. 1. The device 10 comprises a housing 11, with a base 12 and lid 13 connected by hinge 14. The housing 11 may be constructed of suitable plastic material, preferably clear so that the user may view the contents.

The base 12 of the housing defines ridge 15 for engaging lid 13. When the lid 13 is engaged with ridge 15, the device can be shipped prior to use with the contents sterilized or after use for disposal.

Figure 2:
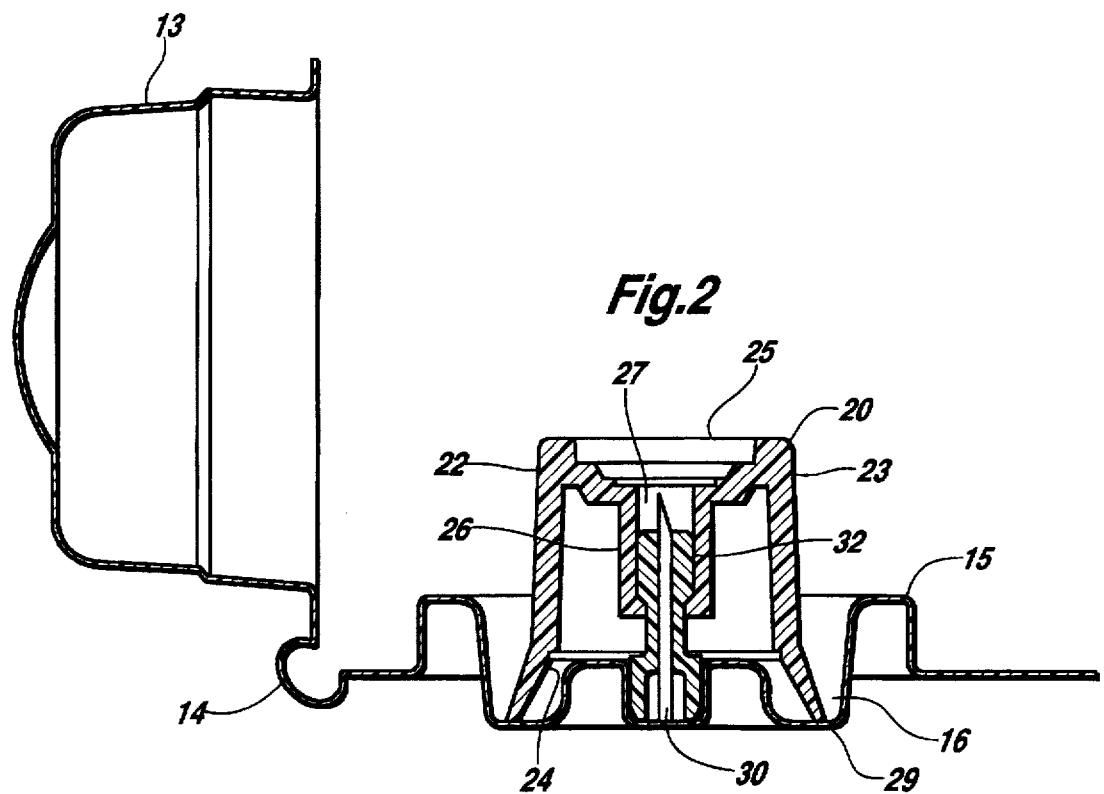
FIG. 2 is a sectional view taken along lines 2—2 of FIG. 1, however, with the top of the container open.

The base 12 of the housing also defines depression 16, as seen in FIG. 2. Depression 16 provides support for cup 20. It also provides support for sterile lancet 30 and bushing 32 which surrounds and vertically supports the lancet 20 on mount 21 in the lancet 30 in depression 16.

Figure 4:
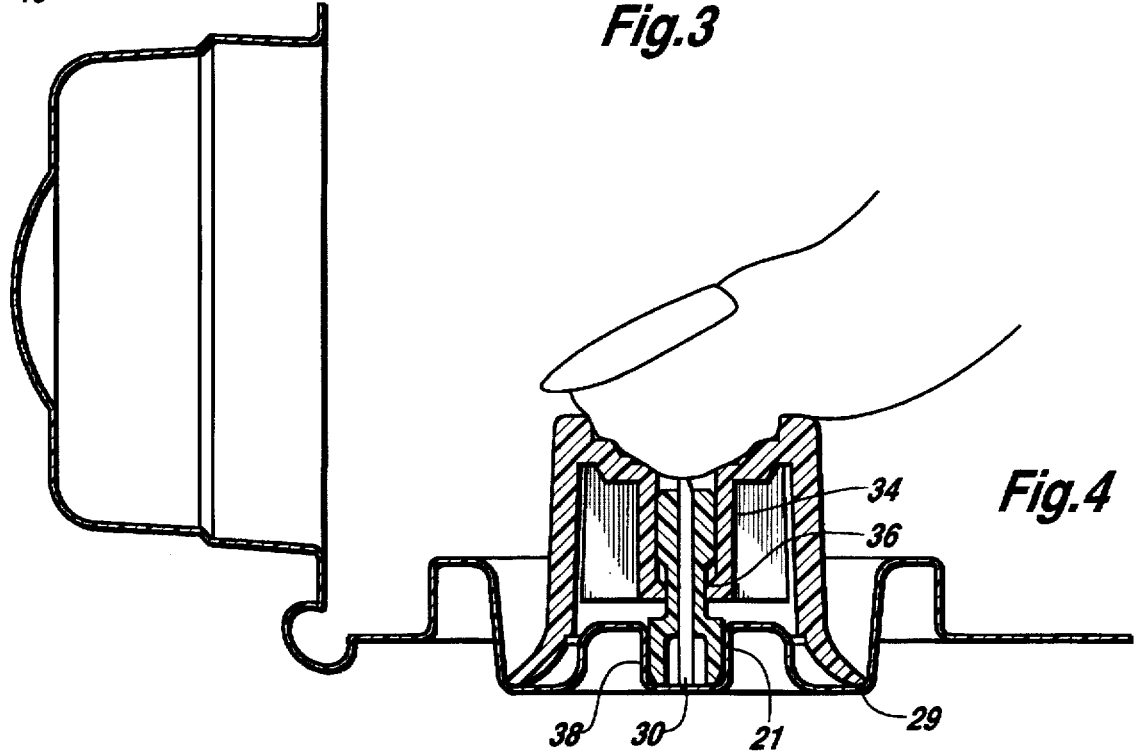
FIG. 4 is a schematic view showing the cup being compressed and used in the practice of the present invention.

Cup 20 is made from a resilient material and comprises top 22, sidewall 23 and bottom 24. The resilient cup is preferably molded from soft durometer rubber like material such as 40–60 durometer silicon rubber. The top 22 of the resilient cup 20 defines opening 25 for placing a finger or skin surface that is intended to be pierced. The opening 25 preferably has shoulders or steps 25a which aid in the placement of the finger, foot or skin surface. Then opening an therefore accommodate adult size fingers as well as those from infants. By placing a finger or skin surface onto opening 25, and pressing downward, the skin is bunched or pinched to increase its surface tension, thereby lessening the pain when the lancet 30, which is directed to the top of the cup, pierces it, as shown in FIG. 4. The bunching or squeezing of the skin causes severe capillary trauma and produces bleeding that is more than adequate for depositing samples on a reagent strip or filter paper. No "milking" or squeezing of the skin is needed to force blood onto the testing medium.

Resilient cup 20 has an inside wall 26 opposite sidewall 23 forming a vertical opening 27 for bushing 32 and lancet 30. Bushing 32 has an enlarged top end 34, narrow neck 36 and enlarged bottom end 38. The vertical opening 27 joins opening 25 at the top 22 of the resilient cup 20. The flexibility and resiliency of cup 20 allows inside wall 26 to move downwardly against bushing 32, particularly the bottom end 38 of the bushing, when cup 20 is compressed and upwardly when the cup is relaxed.

Figure 3:
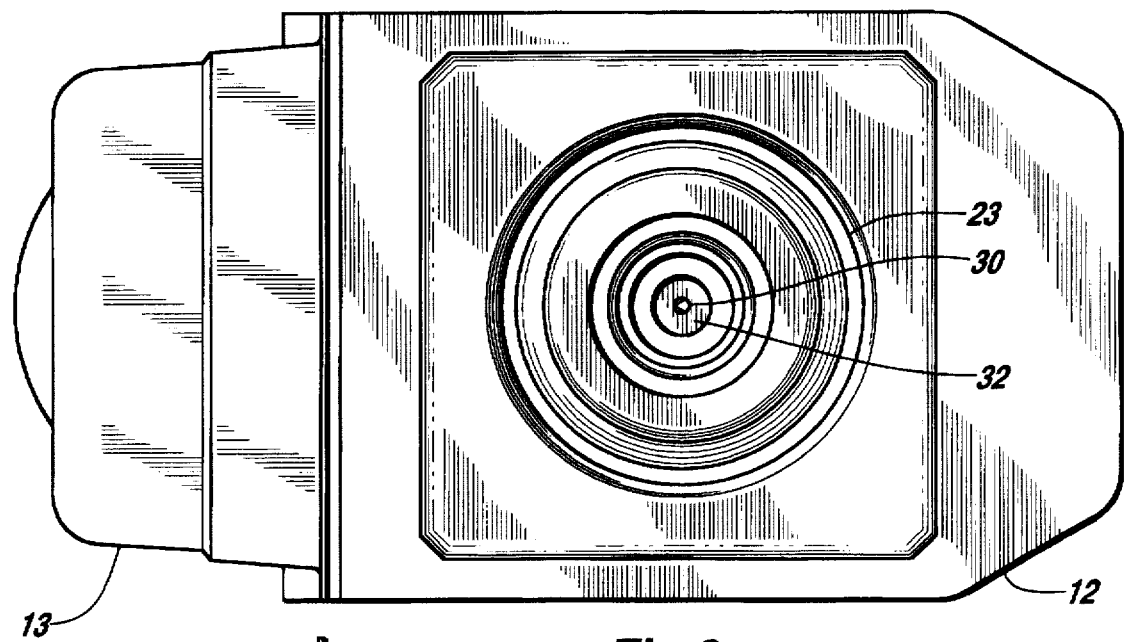
FIG. 3 is a top plan view of the invention.
Figure 5:
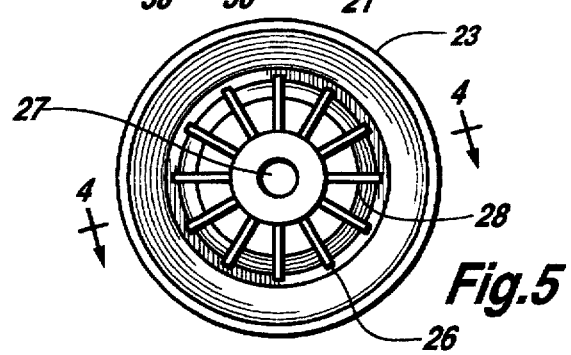
FIG. 5 is a bottom view of the resilient cup of the present invention.

For additional support and to aid in the resiliency of cup 20, there are a plurality of cross-members 28 connecting sidewall 23 as shown in FIG. 5. The cross-members 28 provide resiliency to cup 20 and in conjunction with bushing 32, allow limited penetration of lancet 30 into the finger or skin of the user. The cross members also prevent lateral movement of the lancet 30 and bushing 32. The cup 20 compresses a relatively small area from its first position, a released position, when pressed by a finger due to the networking of cross-members 28 and bushing 32, as shown in FIGS. 2 and 3. In the cup's second position or compressed position, as shown in FIG. 4, the flanged edge 29 of bottom 24 of cup 20 expands outwardly or flattens in depression 16 to absorb the pressure being applied by the finger or skin of the user.

Figures 6A, 6B:
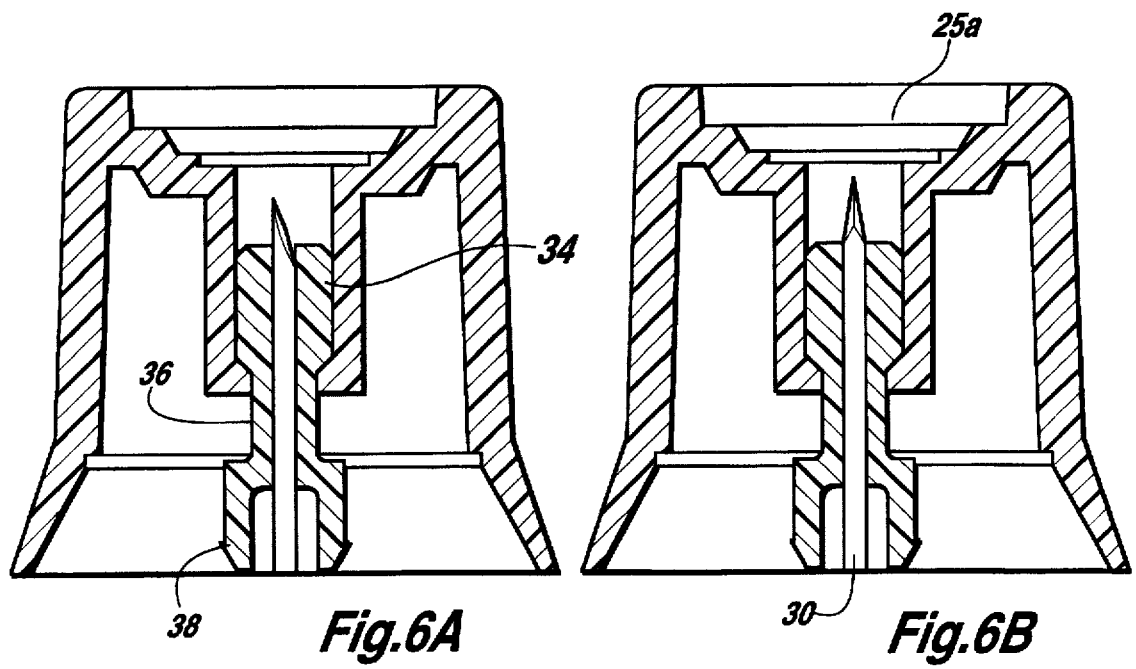
FIG. 6A shows a sectional view of the resilient cup of the present invention.
FIG. 6B is a schematic view of another embodiment of the present invention.
Figure 7:
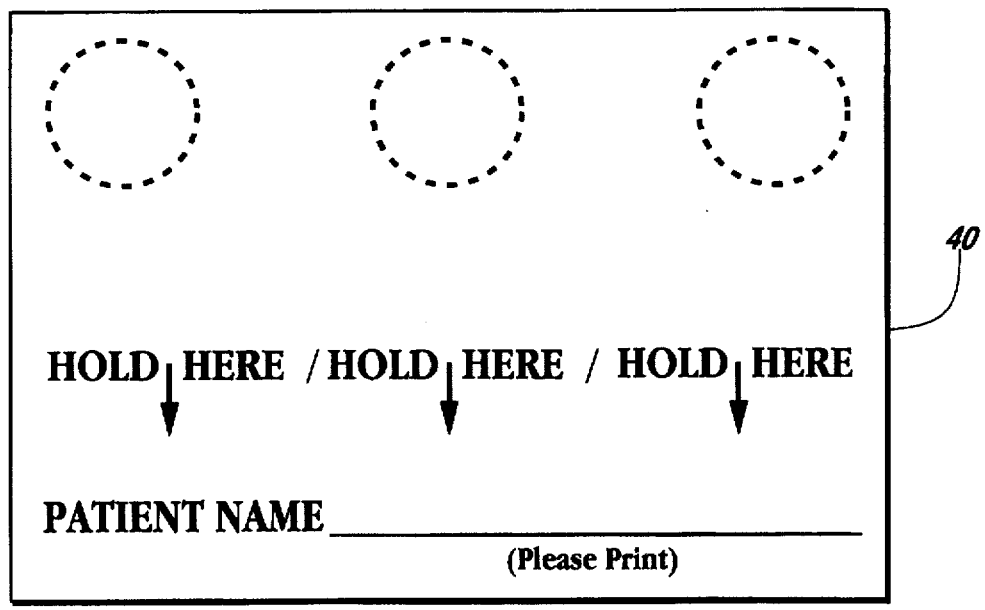
FIG. 7 is a top plan view of filter paper used in the method of the present invention for depositing the blood specimens.

In operation, the user applies a finger or skin surface to top 22, covering opening 25 of resilient cup 20 and presses down. The sidewall 23 and inside wall 26 of the cup 20 compress allowing the inside wall 26 to move downwardly in relation to bushing 32 which supports lancet 30. As compression takes place, flanged edge 29 moves outwardly from sidewall 23 in depression 16. Since only a small portion of the lancet 30 is exposed, as seen in FIGS. 6A and 6B, there is limited penetration of the lancet 30 into the finger or skin. After piercing takes place, the finger or skin surface is removed and the resilient cup 20 is relaxed, allowing inside wall 26 to move upwardly in relation to stable bushing 32 which supports lancet 30 which is rigid. Lancet 30 does not wobble or create lateral movement when compression of cup 20 takes place because of stable support of bushing 32 and its attachment to depression 16. Likewise, cup 20 does not wobble or move laterally when compressed because the cross members 28 provide stability to the cup.

In the preferred practice of the method of the present invention, wherein relatively painless piercing of the skin and blood collection is provided, the skin is first pre-treated with a solution containing an antiseptic agent, such as benzalkonium chloride, and optionally an anesthetic agent such as lidocaine hydrochloride. Preferably, however, no anesthetic is needed since the device of the present invention provides piercing of the skin in a relatively painless manner.

The pretreatment solution might be applied by spraying or with a bandage-like applicator. The solution could contain specific antiviral agents, or general antibacterial—antiviral—antifungal agents such as nonoxynol-9 (Decon Laboratories, Inc.) formalin, etc. The choice of chemical viral inactivator depends on which test will be made on the sample. If desired, a pain depressing agent such as benzocaine or triethanolamine salicylate or a heat stimulating agent like methylsalicylate also may be included along with volatile solvents such as ether. Further, the addition of mild enzyme solutions, such as trypsin, may be useful depending upon the blood component desired to be identified.

The preferred method of piercing the skin, collecting blood components and testing comprises:

STEP 1—applying an antiseptic pretreatment solution with a pad to a portion of the tip of a finger for a few seconds;

STEP 2—removing the protective lid 13 and placing the housing 11 upon a supporting surface;

STEP 3—pressing the tip of the finger lightly on the opening 25 of the cup 20 of the device;

STEP 4—bunching or squeezing the skin within opening by applying pressure to the opening;

STEP 5—piercing the skin by pressing firmly upon the cup 20 with the finger until the resilient cup 20 collapses and lancet 30 pierces the skin and blood flow commences from the pierced skin;

STEP 6—removing the downward pressure on the finger and placing the finger of designated areas on the filter paper 40 and allowing the specimen to drop in the designated area;

STEP 7—wiping the skin area with alcohol or antiseptic; and

STEP 8—providing diagnostic testing to the specimens on the filter paper 40.

Lid 13 can be closed on base 12 and the device 10 may be disposed of.

It will be apparent to those skilled in the art that a number of modifications and changes can be made without departing from the spirit and scope of the invention.

What is claimed is:

1. Blood sampling device comprising;
   A) a base;
   B) a lid hingedly attached to the base;
   C) a resilient cup having a top, bottom which is flexible and expands outwardly upon compression, and side wall mounted on the base;
   D) the top of the resilient cup defining an opening for placing the finger to be lanced
   E) a lancet attached to the base pointed the top of the cup; and
   F) a bushing surrounding the lancet within the flexible cup providing support for the lancet when the resilient cup is compressed.

2. The device described in claim 1 where the resilient cup has a first position when it is relaxed and a second position when it is compressed so that the lancet may pierce a finger or skin placed in the opening on the top of the cup and compressing the cup.

3. The device described in claim 1 wherein the bottom of the cup is flexible and expands outwardly upon compression.

4. The device described in claim 1 wherein the bushing is attached to the base surrounding the lancet.

5. The device described in claim 1 wherein the resilient cup has a wall inside of the sidewall surrounding the bushing, the inside wall and cup being flexible and capable of upward and downward movement.

6. The device described in claim 5 wherein in the first position the inside wall and bottom of the cup are relaxed and in a second position wherein the cup is compressed by a finger or skin surface moving the cup and inside wall downward and expanding the bottom of the cup outwardly allowing the lancet to remain motionless to pierce the skin.

7. The device described in claim 5 wherein a plurality of cross-members connect the side wall and inside wall of the cup providing support to cup.

8. The device described in claim 5 wherein the resilient cup having cross-members connecting the side wall and inside wall, the inside wall operatively associated with the bushing which vertically supports the sterile lancet providing limited penetration into a finger or skin surface compressing the resilient cup.

9. A blood sampling device comprising:
   (a) a base;
   (b) a lid hingedly attached to the base;
   (c) a resilient cup having a top, a bottom which is flexible and expands outwardly upon compression, and sidewall mounted on the base;
   (d) the top of the resilient cup defining an opening for placing a finger or skin to be lanced;
   (e) a lancet attached to the base pointed to the top of the cup;
   (f) a bushing surrounding the lancet within the flexible cup providing support for the lancet when the resilient cup is compressed, the resilient cup having a first position when is relaxed and a second position when it is compressed so that the lancet may pierce the finger to skin placed in the opening on the top of the cup and compressing the cup.

* * * * *